US011391673B2

(12) United States Patent
Bong et al.

(10) Patent No.: US 11,391,673 B2
(45) Date of Patent: Jul. 19, 2022

(54) METHOD FOR PREPARING ENCODED HYDROGEL PARTICLES, AND ENCODED HYDROGEL PARTICLES PREPARED THEREBY

(71) Applicant: Korea University Research and Business Foundation, Seoul (KR)

(72) Inventors: Ki Wan Bong, Seoul (KR); Yoon Ho Roh, Gwacheon-si (KR); Hyun June Moon, Suwon-si (KR); Hyun Jee Lee, Yongin-si (KR); Hyeon Ung Kim, Seoul (KR); Seok Joon Mun, Seongnam-si (KR)

(73) Assignee: Korea Univercity Research and Business Foundation, Seoul (KR)

( * ) Notice: Subject to any disclaimer, the term of this patent is extended or adjusted under 35 U.S.C. 154(b) by 94 days.

(21) Appl. No.: 16/954,642

(22) PCT Filed: Dec. 14, 2018

(86) PCT No.: PCT/KR2018/015898
§ 371 (c)(1),
(2) Date: Jun. 17, 2020

(87) PCT Pub. No.: WO2019/124878
PCT Pub. Date: Jun. 27, 2019

(65) Prior Publication Data
US 2020/0309704 A1    Oct. 1, 2020

(30) Foreign Application Priority Data
Dec. 18, 2017  (KR) .................. 10-2017-0173911

(51) Int. Cl.
*G01N 21/71*   (2006.01)
*C12Q 1/6834*  (2018.01)
*G01N 21/64*   (2006.01)

(52) U.S. Cl.
CPC ....... *G01N 21/6486* (2013.01); *C12Q 1/6834* (2013.01); *G01N 21/71* (2013.01)

(58) Field of Classification Search
CPC ............... G01N 21/6486; G01N 21/71; C12Q 1/6834
See application file for complete search history.

(56) References Cited

U.S. PATENT DOCUMENTS 8,691,754 B2 * 4/2014 Wang ............... G01N 33/54353
                                        514/15.2
8,795,960 B2 * 8/2014 Seul .................... C12Q 1/6809
                                        435/6.1

(Continued)

OTHER PUBLICATIONS

Gaelle C. Le Goff et al., "Hydrogel microparticles for biosensing", European Polymer Journal, 2015, pp. 386-412, vol. 72.
Daniel C. Pregibon et al., "Optimization of Encoded Hydrogel Particles for Nucleic Acid Quantification", Anal. Chem., 2009, pp. 4873-4881, vol. 81.

(Continued)

Primary Examiner — David P Porta
Assistant Examiner — Fani Polyzos Boosalis
(74) Attorney, Agent, or Firm — Sughrue Mion, PLLC

(57) ABSTRACT

The present invention relates to a method for preparing encoded hydrogel particles for high sensitive detection of a target biomolecule with high accuracy, and encoded hydrogel particles prepared thereby and, specifically, to a method for preparing encoded hydrogel particles, comprising a step of synthesizing hydrogel particles, and then binding a probe thereto, and encoded hydrogel particles prepared thereby. According to the present invention, probes can be loaded with remarkably improved high efficiency, loaded probes can be uniformly distributed, and the potential problem of biomolecule detection inhibition caused by an unreacted end can be resolved. In addition, the present invention can be (Continued)

applied to the diagnosis of diseases or screening of drugs through high sensitive multiplex detection of target biomolecules such as nucleic acids and proteins, and therefore, can be widely used in the field of medical diagnosis including molecular diagnosis.

11 Claims, 10 Drawing Sheets

(56) References Cited

U.S. PATENT DOCUMENTS

| | | | |
|---|---|---|---|
| 9,528,145 B2* | 12/2016 | Bisso | C09K 11/7773 |
| 2007/0082019 A1 | 4/2007 | Huang et al. | |
| 2009/0163375 A1* | 6/2009 | Bowman | C12Q 1/6816 |
| | | | 506/9 |
| 2016/0333398 A1 | 11/2016 | Pregibon et al. | |

OTHER PUBLICATIONS

Stephen C. Chapin et al., "Rapid microRNA Profiling on Encoded Gel Microparticles", Angew. Chem. Int. Ed., 2011, pp. 2289-2293, vol. 50.
Seddiki Nesrinne et al., "Synthesis, characterization and rheological behavior of pH sensitive poly(acrylamide-co-acrylic acid) hydrogels", Arabian Journal of Chemistry, 2017, pp. 539-547, vol. 10.
M. S. Shchepinov et al., "Steric factors influencing hybridisation of nucleic acids to oligonucleotide arrays", Nucleic Acids Research, 1997, pp. 1155-1161, vol. 25, No. 6.
David C Appleyard et al., "Bar-coded hydrogel microparticles for protein detection: synthesis, assay and scanning", Nature Protocols, 2011, pp. 1761-1774, vol. 6, No. 11.
Hyewon Lee et al., "Sensitive and Multiplexed on-chip microRNA Profiling in Oil-Isolated Hydrogel Chambers", Angew. Chem. Int. Ed., 2015, pp. 2477-2481, vol. 54.
International Search Report of PCT/KR2018/015898 dated Apr. 8, 2019 [PCT/ISA/210].

* cited by examiner

[Fig. 1]
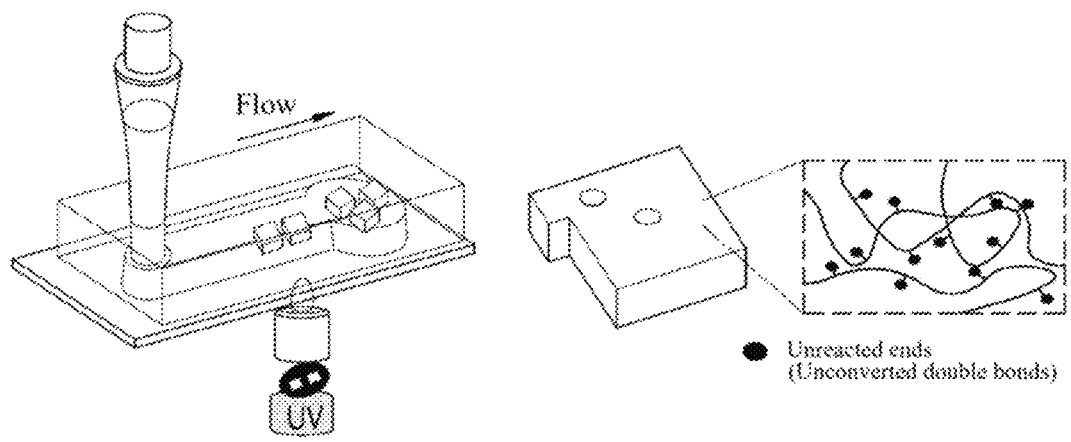
[Fig. 2]
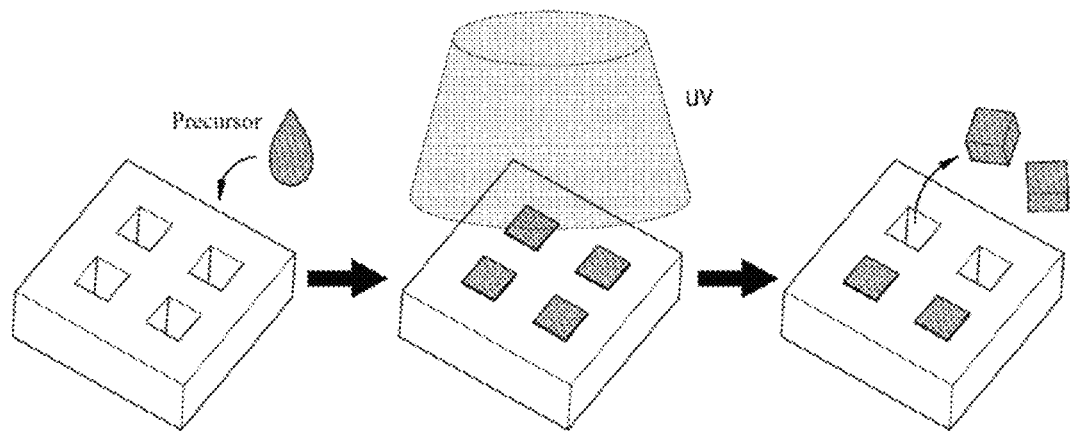

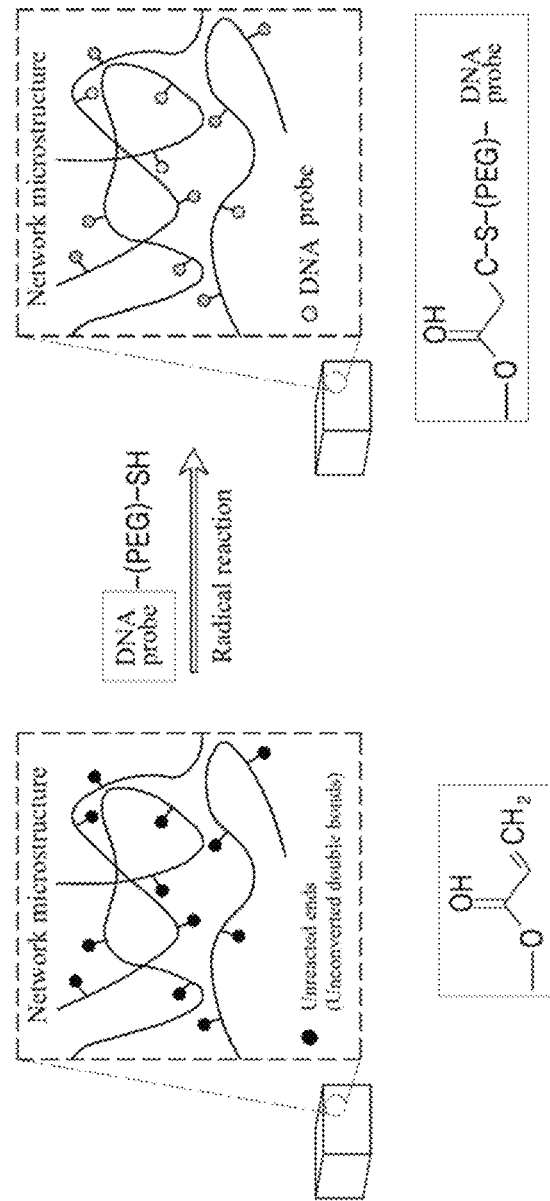
[Fig. 3]

[Fig. 4]
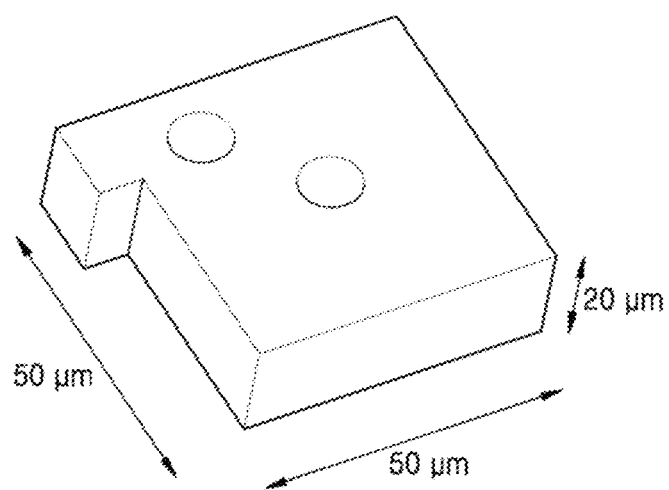
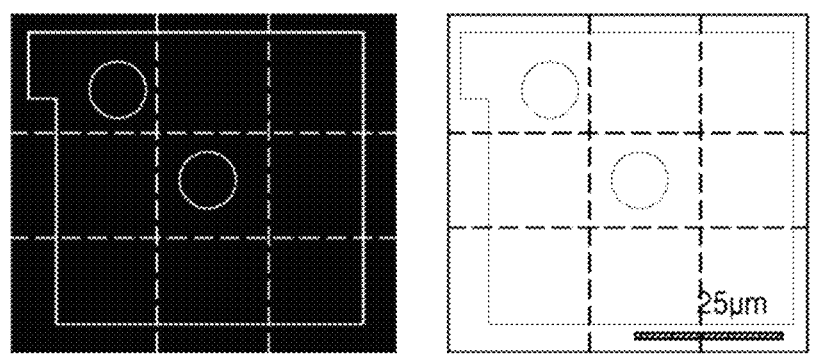

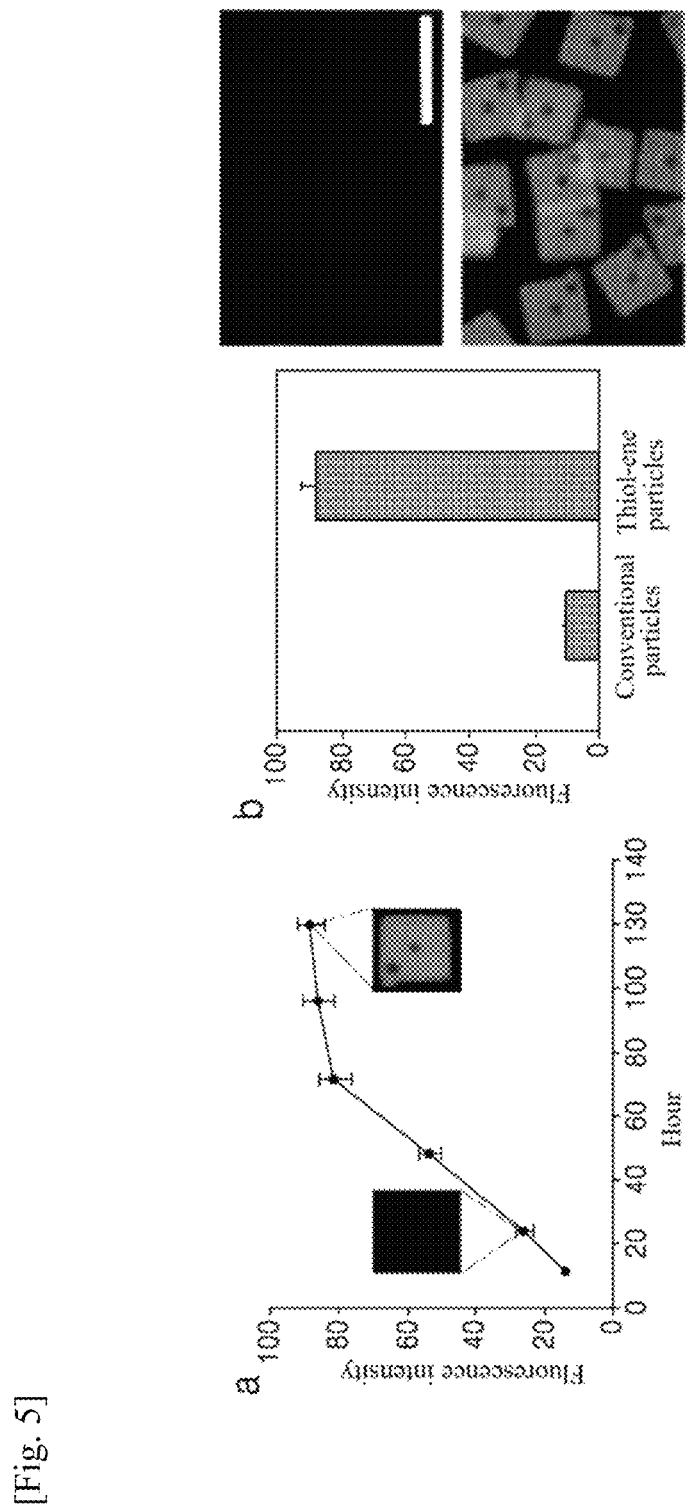
[Fig. 5]

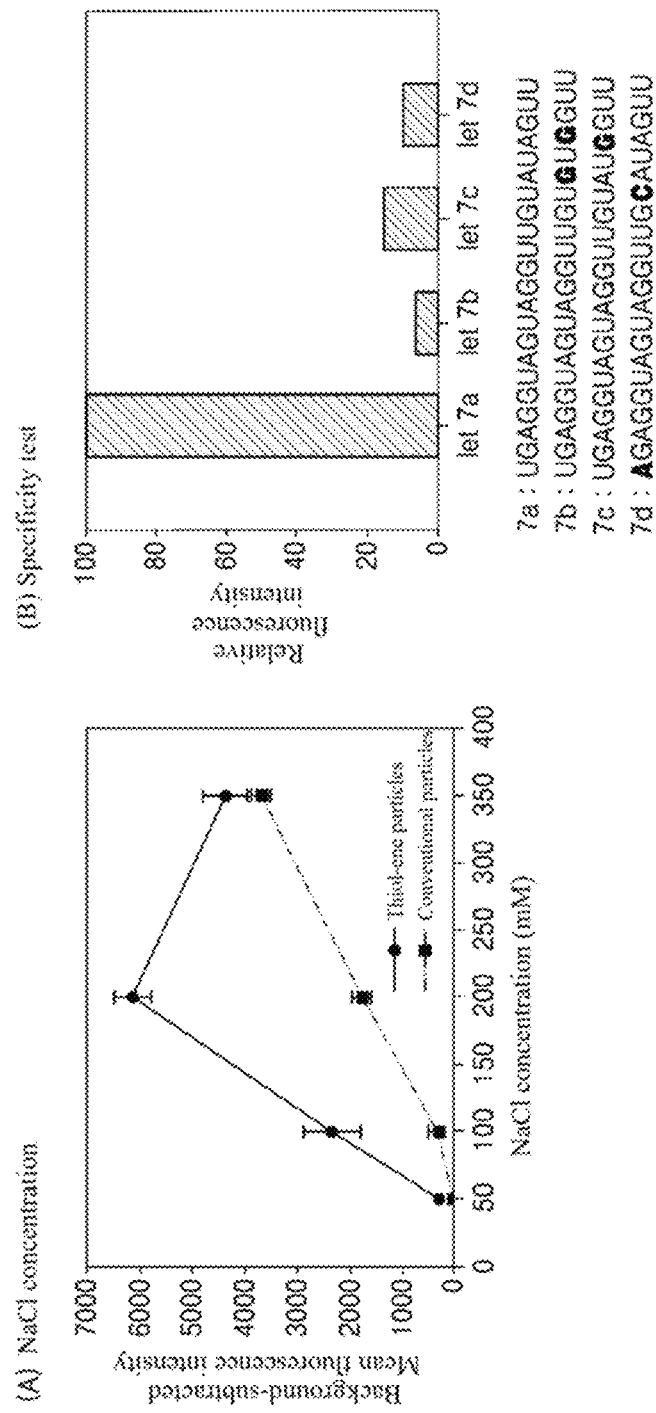
[Fig. 6]

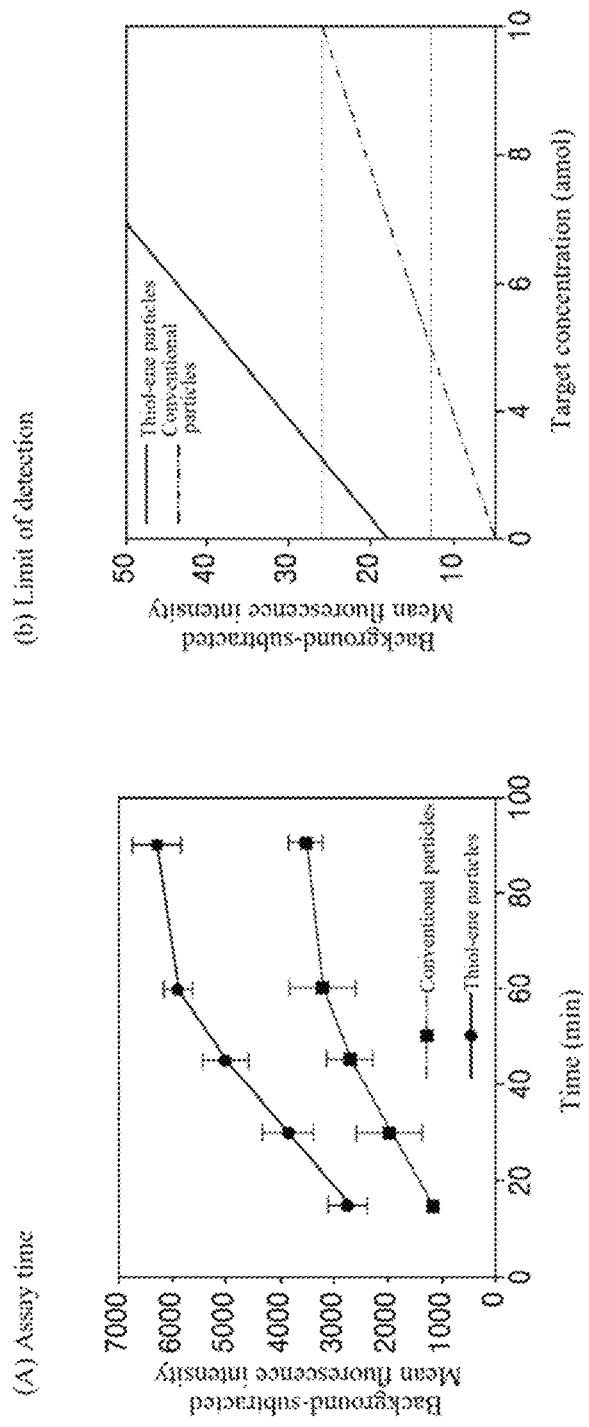
[Fig. 7]

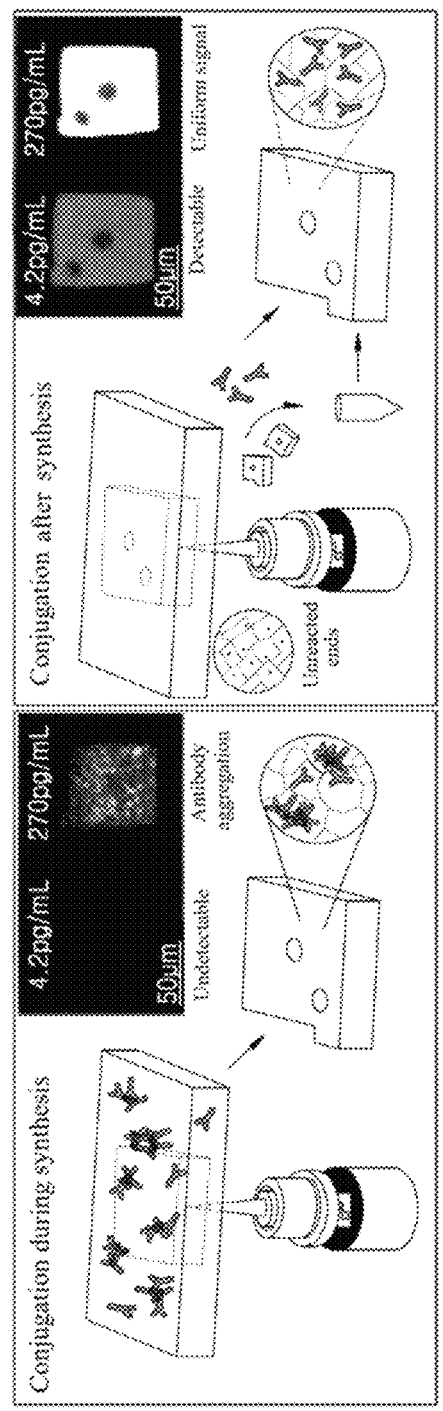
[Fig. 8]

[Fig. 9]
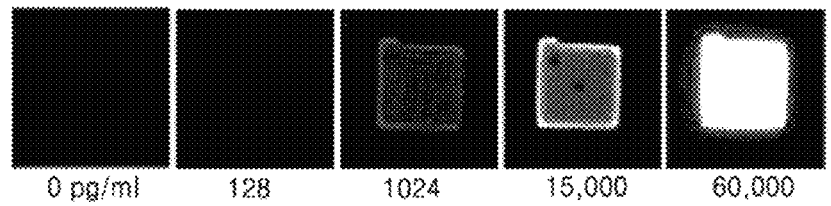
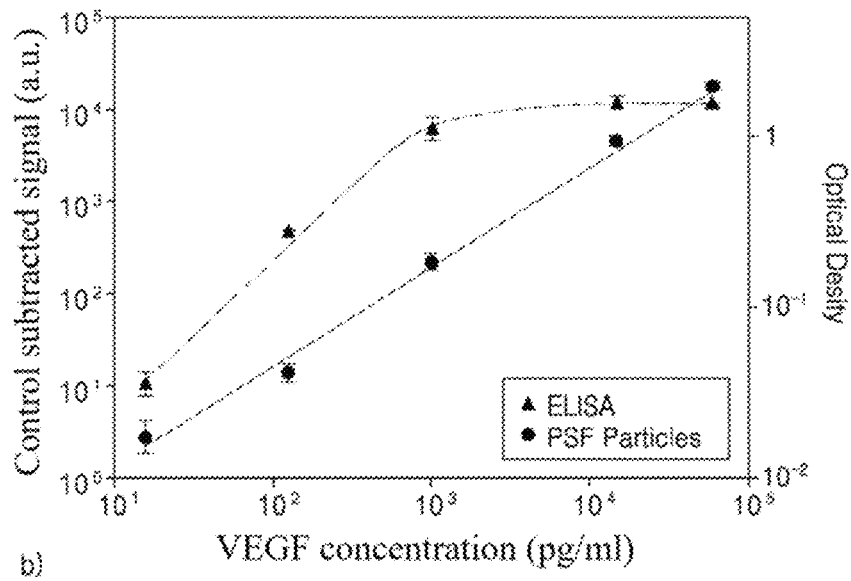
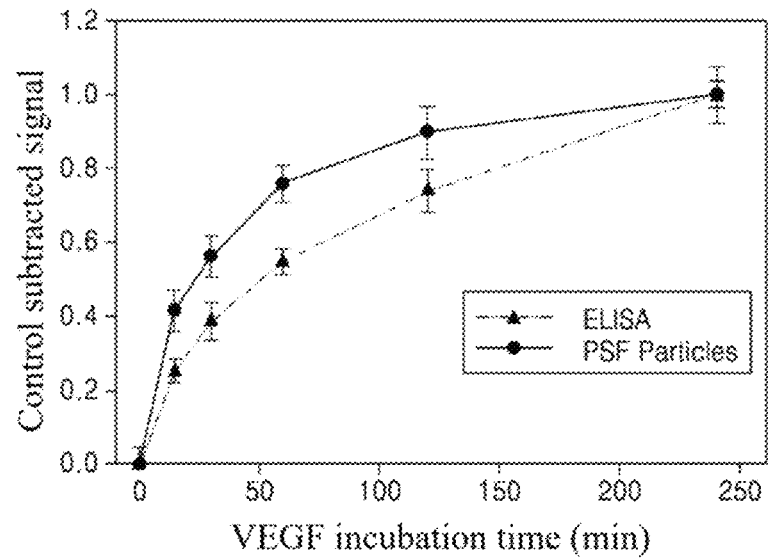

[Fig. 10]
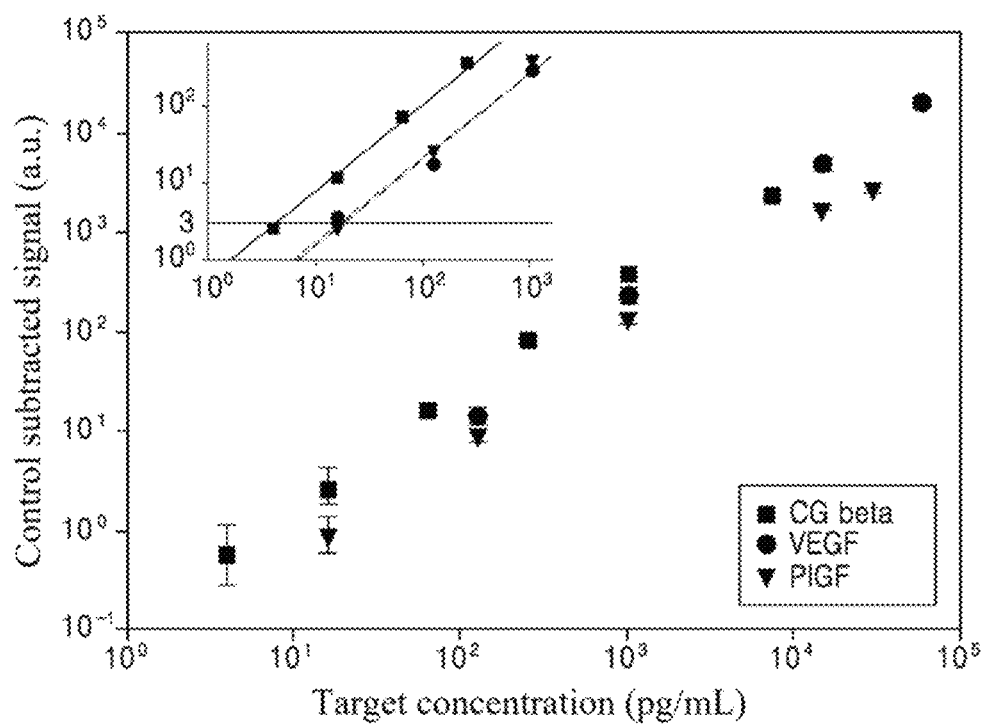

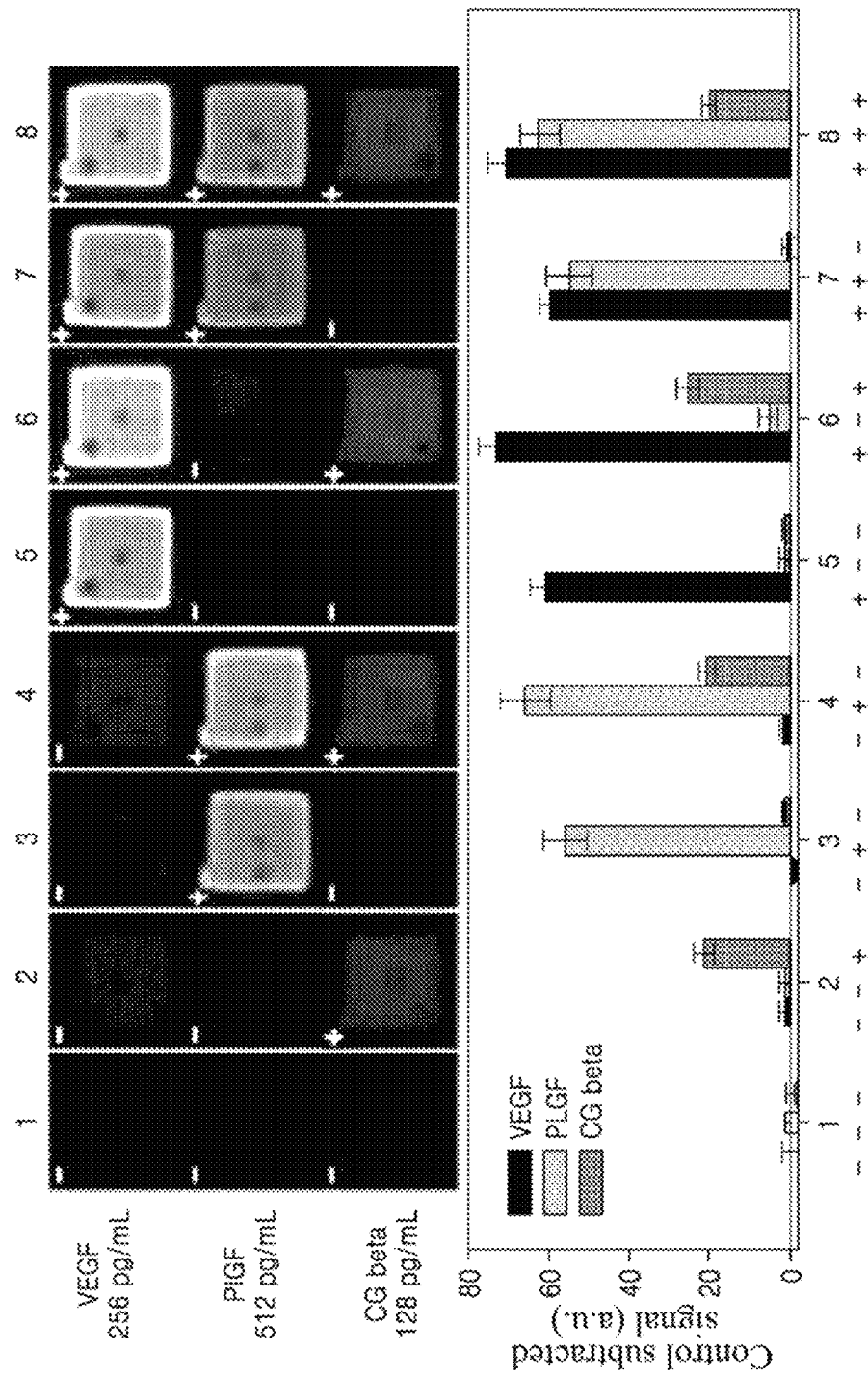
[Fig. 11]

METHOD FOR PREPARING ENCODED HYDROGEL PARTICLES, AND ENCODED HYDROGEL PARTICLES PREPARED THEREBY

CROSS REFERENCE TO RELATED APPLICATIONS

This application is a National Stage of International Application No. PCT/KR2018/015898, filed Dec. 14, 2018, claiming priority to Korean Patent Application No. 10-2017-0173911, filed Dec. 18, 2017.

TECHNICAL FIELD

The present invention relates to a method for preparing encoded hydrogel particles capable of detecting target biomolecules with high accuracy and sensitivity and encoded hydrogel particles prepared thereby. More specifically, the present invention relates to a method for preparing encoded hydrogel particles including synthesizing hydrogel particles and conjugating probes to the hydrogel particles, and encoded hydrogel particles prepared by the method.

BACKGROUND ART

There arises a need to develop techniques for detecting biomolecules such as nucleic acids and proteins with high accuracy and sensitivity in the fields of diagnostics, drug screening, and molecular biochemistry.

Encoded hydrogel particles have attracted much attention as these particles can be used for highly sensitive multiplexed detection of biomolecules. Encoded hydrogel particles include probes loaded to detect biomolecules and codes to identify the loaded probes. The use of encoded particles enables simultaneous capture (i.e. multiplexed detection) of multiple biomolecules in a single detection process and highly sensitive detection of target biomolecules interacting with probes in a three-dimensional particle space.

Flow lithography has received a great deal of attention as a process for synthesizing encoded hydrogel particles with various functions and shapes. Flow lithography allows the synthesis of multifunctional asymmetric particles based on patterning of a microfluidic flow and the use of UV light passing through a photomask. According to flow lithography, a fluid in a microchannel flows without mixing with different adjacent flows due to its low Reynolds number (Re) and can be structured into multiple parallel flows. In addition, patterned UV is irradiated onto a precursor flow through a photomask to induce selective polymerization of the precursor so that particles having the same shape as the photomask can be synthesized. The incorporation of probes such as antibodies and nucleic acids in the precursor enables the synthesis of particles that can be suitable for use in the detection of the biomolecules A conventional method for synthesizing encoded hydrogel particles for the biomolecule detection includes directly mixing a precursor with probes and crosslinking the probes with the particles during the particle synthesis. However, this method suffers from the following problems. Since particles are synthesized within an order of milliseconds by flow lithography, only about 10% of the monomer in the precursor is polymerized, with the result that only about 10% of the probes are crosslinked with the particles. The low loading yield of the probes leads to limited detection performance. Another problem is that most of the probes are not readily dispersed in the precursor. Particularly, when the probes (e.g., antibodies) have low compatibility with the precursor, the precursor should be mixed with the probes for a long time and the probes remaining in the form of aggregates even after mixing may be crosslinked with the particles. In the case where the probes exist in the form of (heterogeneous) aggregates, capture sites for biomolecules are not exposed, resulting in poor detection capability of the probes. Since uniform loading of the largest possible number of the probes is required for highly sensitive detection, the detection performance of conventional method is inevitably deteriorated because of the above-mentioned problems.

As mentioned above, the crosslinking yield of the liquid polymer in flow lithography is as low as about 10%, which leads to the presence of defects on the polymer networks in hydrogel particles. The defects are formed when one of the monomer double bonds remain unreacted in the networks. A considerable number of unreacted reactive groups (unreactive ends or unreactive double bonds) remaining in the final particles are factors deteriorating the ability to detect biomolecules. The unreacted ends can non-specifically bind to target biomolecules to produce a false-positive signal due to their high reactivity. Further, essential materials (e.g., target biomolecules, fluorescent materials, reporters, and cells) to be used during detection react with the unreacted ends and are nonspecifically immobilized on the particles. That is, the presence of the unreacted ends can be a factor deteriorating the ability to detect biomolecules.

Thus, the present inventors have earnestly conducted research to solve the problems of the prior art, and as a result, found that when probes are loaded on encoded hydrogel particles after the particle synthesis, target biomolecules can be detected with high accuracy and sensitivity. The present invention has been accomplished based on this finding.

DETAILED DESCRIPTION OF THE INVENTION

Problems to be Solved by the Invention

One object of the present invention is to provide a method for preparing encoded hydrogel particles including synthesizing hydrogel particles and conjugating probes to the hydrogel particles after the particle synthesis, and encoded hydrogel particles prepared by the method.

Means for Solving the Problems

The present invention provides a method for preparing encoded hydrogel particles including synthesizing hydrogel particles and conjugating probes to the hydrogel particles after the particle synthesis, and encoded hydrogel particles prepared by the method.

The present invention also provides encoded hydrogel particles designed such that code regions are integrated with probe regions.

Effects of the Invention

The method of the present invention ensures loading of probes with significantly improved efficiency and uniform distribution of the loaded probes while avoiding the potential problem that unreacted ends inhibit the detection of biomolecules. By virtue of improved efficiency and uniform distribution of the loaded probes, the encoded hydrogel particles of the present invention can be used for highly sensitive multiplexed detection of target biomolecules such as nucleic acids and proteins. Therefore, the encoded hydrogel particles of the present invention can find application in disease diagnosis and drug screening and can thus be widely used in the field of medical diagnosis such as molecular diagnosis.

Specifically, the method of the present invention enables the conjugation of an at least 8.2-fold larger number of probes to hydrogel particles than conventional methods. In addition, the encoded hydrogel particles of the present invention prevent non-specific binding (false-positive signal) to target biomolecules possibly caused by the presence of unreacted ends, avoid the problem of poor detection performance caused by the non-specific immobilization of essential materials to be used for detection, have increased detection sensitivity to target biomolecules, detect target biomolecules in a short time, have improved specificity for target biomolecules, and have an increased ability to capture target biomolecules.

BRIEF DESCRIPTION OF THE DRAWINGS

FIG. 1 diagrammatically shows a process for the synthesis of hydrogel particles according to the present invention and unreacted ends remaining in the particles after synthesis.

FIG. 2 is a schematic diagram showing a method for synthesizing hydrogel particles by replica molding.

FIG. 3 schematically shows a process for the conjugation of probes with unreacted ends remaining after synthesis of hydrogel particles according to the present invention.

FIG. 4 is a conceptual diagram showing the dimensions and code regions of a hydrogel particle according to the present invention.

FIG. 5 shows time-dependent kinetics for the attachment of probes via a thiol-ene reaction (a) and compares fluorescence signals from conventional particles and thiol-ene particles (particles of the present invention) (b).

FIG. 6 compares fluorescence signals from conventional particles and thiol-ene particles as a function of salt (NaCl) concentration (A) and shows specificity test results (B).

FIG. 7 compares fluorescence signals from conventional particles and thiol-ene particles as a function of incubation time (A) and shows detection sensitivity test results (b). In (b), each of the dashed lines parallel to the X-axis corresponds to 3-fold of the standard deviation of signals from control particles.

FIG. 8 compares the degrees of antibody aggregation on conventional particles and thiol-ene particles.

FIG. 9 compares fluorescence signals from thiol-ene particles and optical densities of ELISA as a function of VEGF concentration a) and shows normalized detection signals from ELISA and thiol-ene particles as a function of incubation time b).

FIG. 10 shows the results of detection sensitivity tests for VEGF, PIGF, and CG beta. The line parallel to the X-axis corresponds to 3-fold of the standard deviation of signals from control particles.

FIG. 11 shows the results of multiplexed detection tests for three different proteins and compares fluorescence signals from thiol-ene particles in a total of 8 cases of the proteins.

BEST MODE FOR CARRYING OUT THE INVENTION

Unless otherwise defined, all technical and scientific terms used herein have the same meaning as commonly understood by one of ordinary skill in the art to which this invention belongs. In general, the nomenclature used herein is well known and commonly employed in the art.

In one aspect, the present invention is directed to a method for preparing encoded hydrogel particles including synthesizing hydrogel particles and conjugating probes to the hydrogel particles after the particle synthesis. The hydrogel particles have available pores whose size is determined such that loading of the probes is facilitated and mass transfer of target biomolecules is ensured.

The probes are conjugated to the synthesized hydrogel particles through unreacted ends remaining in the hydrogel particles. Specifically, the probes are conjugated to the synthesized hydrogel particles through covalent bonds between carbon-carbon double bonds (C=C) of the unreacted ends and functional groups of the probes (FIGS. 1 to 3).

The probes are crosslinked with the synthesized hydrogel particles via a radical reaction and spontaneous electron transfer in a solution. The radical reaction for crosslinking the probes with the synthesized hydrogel particles is initiated by irradiation with UV in the presence of a photoinitiator or by the application of thermal energy in the presence of a thermal initiator. The radical reaction leads to the formation of covalent bonds. Alternatively, the probes may be crosslinked with the synthesized hydrogel particles via electron transfer in a solution. In this case, electrons in an aqueous solution or polar solvent act as nucleophiles to form covalent bonds. Preferably, the probes are crosslinked at a temperature of 0 to 90° C. where the probes can be kept most stable.

The term "probe" as used herein refers to an agent capable of specific binding to a target material in a sample to specifically identify the presence of the target material in the sample.

The probes may include chemically reactive groups that bind to DNA, RNA, proteins or chemical substances including reactive groups for the subsequent incorporation of probes.

The hydrogel particles can be synthesized by various processes such as stop flow lithography (SFL) (FIG. 1) and replica molding (FIG. 2). According to one embodiment of the present invention, the hydrogel particles are synthesized by stop flow lithography (SFL). In this embodiment, a precursor is allowed to flow into a channel or irradiated with UV in the channel. Thereafter, the probes are conjugated to the hydrogel particles to prepare encoded hydrogel particles.

The precursor may include a photocurable monomer containing a methacrylate or acrylate group and a photoinitiator. The photocurable monomer may be, for example, a polyethylene glycol monomer, a 2-methacryloyloxyethyl phosphoryl choline (MPC) monomer or a mixture thereof. The precursor includes a porogen such as polyethylene glycol and/or deionized (DI) water. Alternatively, the precursor may include a plurality of different photocurable monomers.

The encoded hydrogel particles are designed such that code regions are integrated with probe regions. The codes include geometric ones. The geometric codes may consist of combinations of different types of figures. If the design of conventional encoded hydrogel particles such that code regions are separated from probe regions are used, signals from the code regions may overlap detection signals because unreacted ends are distributed over the hydrogel particles. This problem can be avoided by the design of the encoded hydrogel particles according to the present invention in which code regions are integrated with probe regions.

The hydrogel particles may further include functional nanoparticles.

In another aspect, the present invention is directed to encoded hydrogel particles prepared by the method.

In a further aspect, the present invention is directed to encoded hydrogel particles designed such that code regions are integrated with probe regions.

MODE FOR CARRYING OUT THE INVENTION

Examples

The present invention will be explained in more detail with reference to the following examples. It will be appreciated by those skilled in the art that these examples are merely illustrative and the scope of the present invention is not construed as being limited to the examples. Thus, the substantial scope of the present invention should be defined by the appended claims and their equivalents.

Example 1: Synthesis of Encoded Hydrogel Particles, Loading of DNA Probes and Detection of Target microRNAs 1-1: Fabrication of Microfluidic Device A microfluidic device was designed using AutoCAD (Autodesk, USA) and printed on photomask films (Han&All Technology, Korea). The particle was designed to have dimensions of 50 μm (width)×50 μm (length)×20 μm (height) that can be divided into 9 regions to produce bright detection signals for coding (FIG. 4). An SU-8 master mold was generated through photolithography using silicon wafers coated with SU-8 25 (Microchem, USA), which serve as a negative photoresist. The thickness of the SU-8 master including a pattern of the microfluidic device was adjusted to 24 μm. Polydimethylsiloxane (PDMS) (Sylgard 184, Corning, USA) mixed a curing agent at a 10:1 (w/w) ratio was poured on the SU-8 master mold and cured at 70° C. for 8 h. Then, a panel was punched with a biopsy punch (diameter 1 mm) to create holes and the PDMS slab was detached from the SU-8 master and the holes for the introduction of a fluid into the panel. Thereafter, a slide was coated with PDMS and partially cured at 70° C. for 20 min. The PDMS slab was attached to the PDMS-coated slide. Finally, the PDMS device was baked overnight for complete curing.

1-2: Synthesis of Hydrogel Particles

Hydrogel particles were synthesized via stop flow lithography (SFL) (K. W. Bong et al., Lab Chip, 2011, 11, 743-747). Briefly, to perform SFL, a UV light emitting diode (Thorlabs, UK) was used as a light source and a pressure regulator (ITV0031-3BL, SMC pneumatics, Japan) was used to control the flow of a fluid in the microfluidic device. The UV LED and the pressure regulator were controlled in a synchronized manner by a customized circuit board and a LabView (National Instrument, USA) code. Hydrogel particles were synthesized by the UV LED through a film photomask (Hanall Technology, Korea) mounted on an inverted microscope (Axiovert 200, Zeiss, Germany). The particles were synthesized by periodic bursts (50 ms) of UV (4 mW/cm$^2$) when a precursor solution was stopped in the channel during SFL.

The precursor solution was composed of 20% (v/v) polyethylene glycol diacrylate 700 (PEG700DA, Sigma Aldrich, USA), 40% (v/v) polyethylene glycol 600 (PEG200, Sigma Aldrich) as a porogen, 5% Darocur 1173 (Sigma Aldrich) as a photoinitiator, and 35% deionized (DI) water. After synthesis, the hydrogel particles were collected in a microtube pre-filled with 200 μl of a mixture (5×PBST buffer) consisting of 5×PBS buffer (Sigma Aldrich) and 0.05% (v/v) Tween-20 (Sigma Aldrich). The collected particles were vortexed and centrifuged for about 1 min. Then, these microparticles were rinsed by removing 150 μL of supernatant buffer and resuspending in the same volume of fresh 5×PBST. This rinsing step was repeated 5 times. Finally, the hydrogel particles were stored in 140 μL of 5×PBST prior to use.

Hydrogel particles for miRNA detection were synthesized by a conventional method (Y. H. Roh et al., Analyst, 2016, 141, 4578-4586). A precursor solution composed of 20% (v/v) PEG700DA, 40% (v/v) PEG200, 5% (v/v) photoinitiator, and 35% (v/v) 3× Tris EDTA (TE) buffer (Sigma Aldrich) was mixed with an acrydite-modified ssDNA oligomer (Integrated DNA technologies) at a volume ratio of 9:1. Thereafter, hydrogel particles were prepared under the same UV intensity and exposure time conditions as above.

1-3: DNA Probe Loading ssDNA probes were immobilized on the hydrogel particles using the thiol-ene Michael addition reaction. A thiol-modified ssDNA oligomer (Integrated DNA technologies, USA) was reduced in 0.5 M tris[2-carboxyethyl]phosphine (Thermo Fisher Scientific, USA) to form active sulfhydryl groups. Thereafter, the reduced oligomer was mixed at a concentration of ~7 particles/μL with the hydrogel particles suspended in 140 μL of a buffer. The final mixed solution was incubated in a thermal shaker (Thermoshaker, Hangzhou Allsheng Instruments Co. Ltd, China) at a constant temperature of 37° C. with agitation at 1,500 rpm. Nuclease-free water, autoclaved pipet tips and microtubes were used to prevent potential contamination.

1-4: miRNA Detection Assay miRNA detection assays were carried out in a total volume of 50 μL. First, 40 μL 1×TET buffer composed of 1× TE buffer (Sigma Aldrich) and 0.05% (v/v) Tween-20 was applied to each microtube, followed by adding 5 μL of target miRNAs. The detection sensitivity of the miRNA assays was evaluated by varying miRNA and NaCl concentrations and hybridization times. The mixture was heated to 95° C. for 5 min in a thermal shaker. After cooling to room temperature, the probe-loaded hydrogel particles and conventional hydrogel particles (~50 particles per target) were added to the microtubes. The assay microtubes were incubated at 55° C. for 15-90 min in the thermal shaker with agitation at 1500 rpm in order to allow for hybridization of the target miRNAs with probes in the hydrogel particles.

To observe the effect of the NaCl concentration, the final concentration of NaCl in the hybridization buffer was adjusted to 50-350 mM. The assay was conducted at 55° C. for 90 min. After the hybridization, the hydrogel particles were rinsed three times with 350 μL of 1×TET containing 50 mM NaCl, and then 245 μL of a ligation mixture was added. This ligation mixture was composed of 1350 μL 1×TET, 150 μL 10× NE Buffer 2 (New England Biolabs, USA), 250 nM ATP (New England Biolabs), 40 nM universal adapter (Integrated DNA technologies), and 800 U ml$^{-1}$ T4 DNA ligase (Thermo Fisher Scientific). Then, the mixture was hybridized at 21.5° C. for 45 min in a thermal shaker. After another rinsing step, streptavidin-phycoerythrin (SA-PE; Life Technologies, USA), diluted in 1×TET by a factor of 10, was added. A final incubation step was allowed at 21.5° C. for 45 min. After the rinsing step, 50 μL of the hydrogel particles suspension in the 1×TET was used for image analyses.

1-5: Image Analysis

RGB fluorescence images of hydrogel particles were acquired using a digital single-lens reflex (DSLR) camera (EOS 6D, Canon, Japan). For monochrome fluorescence images to analyze the intensity of the target signal from the probe region, a scientific complementary metal-oxide-semiconductor (sCMOS) camera (Prime, Photometrics, USA) was used. Both cameras were connected to an inverted microscope (Axiovert 200, Zeiss). An LED lamp (HXP 120 V, Zeiss) was filtered through a cube set for imaging the particles. To obtain signals at various analysis times and NaCl concentrations, 4.5 mW/cm$^2$ LED intensity with 1000 ms exposure time was used. For analysis sensitivity measurement, 11 mW/cm$^2$ LED intensity with 300 ms exposure time was used. The monochrome fluorescence images were analyzed by Image J software (National Institute of Health, USA).

1-6: Assay Results

An at least 8.2-fold larger number of the probes (single strand DNAs) were conjugated in the encoded hydrogel particles (hereinafter referred to as "thiol-ene particles") prepared by synthesizing the hydrogel particles and loading the probes on the hydrogel particles compared to in encoded hydrogel particles (hereinafter referred to as "conventional particles") prepared from a precursor containing probes according to a conventional method (FIG. 5).

Nucleic acids were detected by varying the concentrations of NaCl from 50 mM to 350 mM. The analysis revealed that the detection sensitivity increased but the detection specificity decreased with increasing NaCl concentration. Unlike the conventional particles, the thiol-ene particles produced an optimal signal at a low NaCl concentration (200 mM) ((A) of FIG. 6).

Specificity tests were conducted using the same procedure of the miRNA detection, except that the initial amount of 1×TET was 25 μL, four microRNAs (let-7a, let-7b, let-7c, and let-7d) were added in amounts of 1000 amol, and the NaCl concentration was 200 mM. As a result, the maximum cross-reactivity was reduced from 25% to 15% ((B) of FIG. 6).

The assay was conducted by varying the assay time for nucleic acid detection. The analysis revealed that the thiol-ene particles produced the same fluorescence signal at an at least 3-fold higher rate than the conventional particles ((A) of FIG. 7).

The initial amount of 1×TET was adjusted to 40 μL, signals were detected by spiking-in 50, 100, 500, 1000, and 5000 amol of the conventional particles and the thiol-ene particles with NaCl concentrations of 350 mM and 200 mM, respectively, and thereafter, the limits of detection were obtained by extrapolating the plots of the fluorescence signals versus the target concentration. As a result, the limit of detection of the thiol-ene particles (3.4 amol) was lower than that of the conventional particles (4.9 amol) ((b) of FIG. 7).

For protein detection, antibodies were susceptible to aggregation in the conventional particles due to poor compatibility with the precursor, whereas no antibody aggregation was observed in the thiol-ene particles, leading to an increase in detection sensitivity (FIG. 8).

Example 2: Synthesis of Encoded Hydrogel Particles, Loading of Antibody Probes and Detection of Target Proteins 2-1: Fabrication of Microfluidic Device A microfluidic device for the synthesis of hydrogel particles was fabricated by the same method described in Example 1.

2-2: Synthesis of Hydrogel Particles and Loading of Antibody Probes

Particle synthesis and probe loading were carried out in two discrete steps. The precursor solution consisted of 20% (v/v) polyethylene glycol diacrylate 700 (PEG700DA, Sigma Aldrich, USA), 40% (v/v) polyethylene glycol 600 (PEG200, Sigma Aldrich) as a porogen, 5% Darocur 1173 (Sigma Aldrich) as a photoinitiator, and 35% deionized (DI) water. One cycle of particle synthesis via stop flow lithography consisted of 400 ms of flow, 200 ms of stop, 75 ms of UV exposure, and 200 ms of hold time. For each protein assay, 1 h synthesis produced around 4000 particles using a 1-D photomask. Different photomasks were used to synthesize particles for the detection of different proteins. After synthesis, particles were washed three times in 1×PBST. For antibody attachment to the particles, 16.5 μL of particles (55 particles/μL) were incubated with 12 μL of the reconstituted capture antibody (6 μg/μL for IL-6, 3 μg/μL for VEGF, 12 μg/μL for PIGF, and 3 μg/μL for CG beta) and 1.5 μL of heterobifunctional PEG linker (Thiol-PEG2000-NHS, Nanocs) for 48 h at 1500 rpm at 25° C. Based on the finding that the isolation of steps did not produce any discernible advantage, functionalization of antibodies and their immobilization on the particles were performed in a single step to reduce the number of steps as well as the preparation time. After antibody attachment, the particles were washed three times in 1×PBST.

2-3: Protein Detection

For protein detection, 50 particles in 25 μL 1×PBST and 25 μL of 2× target protein in 2% BSA in 1×PBS were placed in a microtube. The particles were incubated for 2 h at 1500 rpm at 25° C. After rinsing three times in 1×PBST, 10 μL of the reconstituted secondary antibody (12.5 ng/μL for IL-6, 25 ng/μL for VEGF, 15 ng/μL for PIGF, and 125 ng/μL for CG beta) was added to the protein-bound particles in 40 μL 1×PBST. The mixture was incubated for 1 h at 1500 rpm at 25° C. After three washes in 1×PBST, 10 μL of streptavidin-phycoerythrin (SA-PE, Life Technologies), diluted in 5% BSA in 1×PBST by a factor of 50, was added to the particles in 40 μL 1×PBST. The mixture was incubated to fluorescently label the antibodies. The particles were rinsed five times with 1×PBST before imaging.

2-4: Image Analysis

The same system described in Example 1 was used for image analysis. The images were taken with an exposure time of 50 ms. The intensity of the light source was fixed at 1100 mW/cm$^2$. The fluorescence intensity of the images retrieved in TIFF format was measured using an Image J program.

2-5: ELISA

The procedure followed the general ELISA protocol provided by the manufacturer. A 96-well microplate (R&D Systems) was coated with 100 μL per well of diluted VEGF capture antibody (1 μg/ml) and incubated overnight at 25° C. The wells were rinsed three times with 400 μL of 1×PBST. To block free sites, the plate was incubated for 1 h with 300 μL of 1% BSA in 1×PBS. After two washes, the plate was incubated for 2 h with 100 μL of the target protein diluted in 1% BSA in 1×PBS. The wells were washed three times before 100 μL of the diluted detection antibody (100 ng/ml) was added. The plate was incubated for 2 h at 25° C. After three washes, 100 μL of 40-fold diluted streptavidin-HRP (R&D Systems) was added to each well and incubated for 20 min. The plate was washed three times, and 100 μL of substrate solution (R&D Systems, cat. no. DY999) was added and incubated for 20 min at 25° C. After adding 50 μL of stop solution (R&D Systems, cat. no. DY994), the optical density was determined using a microplate reader (Spectra-Max iD5, Molecular Devices) set to 450 nm and 570 nm. The readings at 450 nm were subtracted from the readings at 570 nm to correct for optical imperfections in the plate.

2-6: Multiplexed Detection

Multiplexed detection was performed for a total of 8 cases. In each case, 150 particles (50 per protein) in 100 μL 1×PBST were mixed with 100 μL of 2× target proteins in 2% BSA in 1×PBS. The pre-mixture was prepared by mixing 25 μL of 2% BSA in 1×PBS with 25 μL 8× target protein in 2% BSA in 1×PBS for target presence and 25 μL of 2% BSA in 1×PBS for target absence. The particles in 8 different target combinations were incubated for 2 h at 1500 rpm at 25° C. The particles were washed three times in 1×PBST and 10 μL of each of the three secondary antibodies (25 ng/μL for VEGF, 15 ng/μL for PlGF, and 125 ng/μL for CG beta) were added to the particles in 20 μL 1×PBST. The mixtures were incubated for 1 h at 1500 rpm at 25° C. After three washes in 1×PBST, the secondary antibodies were fluorescently labeled by adding 30 μL of streptavidin-phycoerythrin diluted in 5% BSA in 1×PBST by a factor of 50 to the particles in 120 μL 1×PBST. The particles were washed five times in 1× PBST before imaging.

2-7: Assay Results

According to the conventional method for preparing encoded hydrogel particles from a precursor containing probes, the presence of a hydrophobic initiator caused antibody aggregation. In contrast, the method of the present invention for preparing encoded hydrogel particles by synthesizing hydrogel particles and loading probes on the hydrogel particles prevents antibody aggregation and ensures uniform conjugation of the probes to the particles (FIG. 8).

In the comparative experiments with ELISA, which is a procedure usually used for protein detection, the thiol-ene particle assay had a detection range of 17.7-60000 pg/mL, resulting in a 3.5 log range compared to ELISA having a detection range of 31.2-2000 pg/mL, resulting in a 1.8 log range. The lower limit of detection (17.7 pg/ml) demonstrated greatly improved performance of the thiol-ene particle assay compared to ELISA (a) of FIG. 9).

The normalized fluorescence signals of ELISA and the thiol-ene particle assay were observed as a function of incubation time. As a result, a little less than 1 h incubation in the thiol-ene particle assay produced a signal that is comparable to 2 h incubation in the ELISA (b) of FIG. 9).

To obtain calibration curves of three proteins (VEGF, PlGF, and CG beta), the proteins were spiked-in at different concentrations to detect signals and the plots of the fluorescence signals versus the protein concentration were then extrapolated to determine the limits of detection. As a result, the limits of detection (LODs) were 17.7, 17.5, and 4.2 pg/ml for VEGF, PlGF, and CG beta, respectively (FIG. 10).

To confirm whether multiplexed detection of the three proteins was feasible, a total of eight cases depending on the presence or the absence of the protein were used. Multiplexed detection was successfully performed in all cases (FIG. 11).

Although the particulars of the present disclosure have been described in detail, it will be obvious to those skilled in the art that such particulars are merely preferred embodiments and are not intended to limit the scope of the present invention. Therefore, the true scope of the present invention is defined by the appended claims and their equivalents.

INDUSTRIAL APPLICABILITY

The method of the present invention ensures loading of probes with significantly improved efficiency and uniform distribution of the loaded probes while avoiding the potential problem that the detection of biomolecules can be inhibited by unreacted ends. In addition, the encoded hydrogel particles of the present invention can be used for highly sensitive multiplexed detection of target biomolecules such as nucleic acids and proteins. Therefore, the encoded hydrogel particles can find application in disease diagnosis and drug screening and can thus be widely used in the field of medical diagnosis such as molecular diagnosis.

The invention claimed is:

1. A method for preparing encoded hydrogel particles comprising:
synthesizing hydrogel particles including code regions for identifying a probe; and conjugating probes to the hydrogel particles,
wherein the probes are conjugated to the synthesized hydrogel particles through covalent bonds between carbon-carbon double bonds (C=C) of unreacted ends remaining in the hydrogel particles and functional groups of the probes.

2. The method according to claim 1, wherein the probes are crosslinked with the synthesized hydrogel particles via a radical reaction and spontaneous electron transfer in a solution.

3. The method according to claim 2, wherein the radical reaction for crosslinking the probes with the synthesized hydrogel particles is initiated by irradiation with UV in the presence of a photoinitiator or by the application of thermal energy in the presence of a thermal initiator.

4. The method according to claim 2, wherein when the probes are crosslinked with the synthesized hydrogel particles via electron transfer in a solution, electrons in an aqueous solution or polar solvent act as nucleophiles to form covalent bonds.

5. The method according to claim 2, wherein the probes are crosslinked at 0 to 90° C.

6. The method according to claim 1, wherein the probes are DNA, RNA or proteins.

7. The method according to claim 1, wherein the encoded hydrogel particles are designed such that code regions are integrated with probe regions.

8. The method according to claim 7, wherein the codes comprise geometric ones.

9. The method according to claim 8, wherein the geometric codes consist of combinations of different types of figures.

10. The method according to claim 1, wherein the hydrogel particles further comprise functional nanoparticles.

11. Encoded hydrogel particles prepared by the method according to claim 1.

* * * * *